United States Patent [19]
Patel et al.

[11] Patent Number: 6,073,046
[45] Date of Patent: Jun. 6, 2000

[54] HEART MONITOR SYSTEM

[76] Inventors: Bharat Patel, 17448 Hwy. 3 Suite 275, Webster, Tex. 77598; Karim Alhussiny, 1307 Dalerose Ct., Houston, Tex. 77062

[21] Appl. No.: 09/067,199

[22] Filed: Apr. 27, 1998

[51] Int. Cl.[7] .............................. A61B 5/04; A61B 5/0402
[52] U.S. Cl. .......................... 600/509; 128/903; 128/904; 600/512
[58] Field of Search .................................... 600/509, 512; 128/903, 904

[56] References Cited

U.S. PATENT DOCUMENTS

| | | | |
|---|---|---|---|
| 3,724,455 | 4/1973 | Unger | 128/903 |
| 4,751,726 | 6/1988 | Hepp et al. | |
| 4,889,134 | 12/1989 | Greenwold et al. | |
| 4,987,897 | 1/1991 | Funke | |
| 5,381,798 | 1/1995 | Burrows | |
| 5,694,940 | 12/1997 | Unger et al. | |
| 5,832,490 | 11/1998 | Riley | 707/101 |

*Primary Examiner*—William E. Kamm
*Assistant Examiner*—Carl H. Layno
*Attorney, Agent, or Firm*—Gunn & Associates, P.C.

[57] ABSTRACT

A medical facility after discharge of a cardiovascular patient, can remain in contact with the patient. The patient is provided with a multiple lead EKG terminal spread placed on the body, and the signals therefrom are collected and transmitted. They are transmitted to a remote central location. At the central location, the transmitted EKG data is analyzed. It is compared with normal EKG signals and signals captured in time from the same patient as part of the patient history. The evaluation is done through a neural network which forms an output signal automatically or through intervention of a cardiologist sending an alarm condition signal to the patient instructing the patient to get immediate treatment at the patient's location or to otherwise go to a specific medical facility. Signal preparation includes providing EKG signals through a multiplexer, conversation into a digital data, removal of bias signals, stabilization of this EKG base line, compression and data transmission through a modulator. The receive signal is reconstructed to provide an EKG signal of the patient which is then evaluated in the neural network. As appropriate, transmitter/receiver repeater stations and synchronous satellites are used to convey these signals.

44 Claims, 4 Drawing Sheets

HEART MONITOR SYSTEM

BACKGROUND OF THE DISCLOSURE

Heart related disorders resulting from lack of coronary circulation, such as a heart attack, have been and likely will continue to be the most common cause of death in the industrialized world. An estimated 3–4 million Americans suffer from heart attack per year. Approximately half of the heart attacks are "silent" meaning they are not felt by patients. Half of the patients who sustain heart attacks die prior to arrival to hospital. The present innovation, therefore, relates to early detection and long term monitoring of heart related disorders.

There are any number of patients who are suspected of heart disease. As the effects of aging manifest in the population in general, certain heart ailments will sometimes appear suddenly, or will sometimes develop slowly over a period of time. Beginning at about age 50 for men and age 60 for women, it is usually desirable to build a data base line by conducting an annual physical which includes the collection of at least some heart data. A resting electrocardiogram (EKG) typically done with three leads provides modest data. It is much more desirable to obtain data with a twelve lead EKG test, and even better to obtain the test data on a stress test utilizing a treadmill. Any number of specific protocols have been developed for conducting the stress treadmill test and obtaining data from it. Technically, the heart attack is often defined as myocardial infarction (MI) and typically involves a localized shortage of oxygen or the formation of a regionalized blood clot which attributes to a shortage of oxygen in some portion of the heart. These conditions are known as ischemia and thrombosis. With age and perhaps a loss of cardiovascular strength, a patient may develop difficulties which can be observed b y listening, but the better approach is the collection of data with a multiple lead EKG test. The multiple lead approach simply gathers so much more data that it is much easier to measure both an initial state of affairs and to make prompt appraisal of the condition of the patient.

In any number of situations, heart patients may have a series of difficulties over time. With each small or large difficulty, there will be some change in the base line conditions for that patient. While some measure of recovery can be had, the prevailing or normal circumstances for that patient will be, in some fashion, different than they were when that patient was just becoming an adult. So to speak, each event may define or redefine the base line circumstances.

In other instances, no base line data will be available because the patient will be suddenly struck with difficulties or an ailment with results something less than fatal. Nevertheless, the ailment impacts the patient, perhaps requiring treatment for a day or two and some hospitalization. Consider, for example. a middle aged person who has a modest chest pain and is immediately admitted to a hospital for observation. They may leave the hospital the next day, perhaps with medications and with warnings, perhaps dire or otherwise, demanding a change in lifestyle including a new diet, reduction of stress, and other changes in lifestyle. Instructions to return to the doctor in a few days represents some sort of cold comfort which they carry with them. The return to the doctor is normally for the purpose of simply monitoring their condition. Usually, the medical personnel in charge of treatment have a fairly safe estimation of risk and health maintenance that are necessary for the patient. The patient, however, is normally struck with fear and apprehension. Moreover, for many types of ailments, merely going to a doctor's office and especially doing to a hospital prompts a high level of internalized stress which is manifest in the cardiovascular system. Some people become highly agitated which is reflected in an elevated pulse rate, perhaps shallow breathing and other common symptoms of stress. These make the return visits to the doctor somewhat problematic. It makes it difficult at any point in time for medical intervention in that the patient is asked to calm their stress and lay aside the worries and anxieties, both real and imagined, of the next episode. They always question whether the next episode will be small or large, sudden or immediate. It is fair to say that this possibly short term stress and anxiety affects the collection of the cardiovascular data, and may even mask or otherwise perturb more permanent cardiovascular indicators.

Interestingly, the collection of cardiovascular data on a long term basis enables the patient to return in some fashion to a normative lifestyle. Stress and related anxiety are generally reduced. Furthermore, not hearing the truth somehow avoids the bad news, and subject to this thinking, many patients are rebellious about return to the doctor and will not return. They reason along the lines that the knowledge will be frightening so that if they do not know, a cardiovascular abnormality will somehow not harm them. The dangers in this attitude are conspicuous.

A relatively high level of anxiety is manifest by a patient who is required to undergo a stress treadmill test. Not only is there physical stress in the sense that muscles are pushed to the limit, but there is simply the anxiety that this is a test not required of healthy people. By contrast, when a patient is monitored day and night, they are compelled to forget the monitoring. Monitored data will, therefore, reflect long term conditions and not be perturbed by short term, testing related emotional effects.

The monitoring of a patient around the clock, however, is clumsy because of the nature of the equipment. One common monitoring system involves the Halter test. This test involves recording, in a small cassette recorder, heart data which is derived from a few EKG leads where the data are recorded on a cassette. Typically, this test is applied to a patient for only 24 hours. One aspect of the test that is burdensome is that the patient must report back to the doctor's office, return the equipment and deliver the cassette. Thereafter, the cassette has to be played back on a magnetic tape deck, signals presented on a screen, and the signals inspected on the screen. In the past, this data processing has been done by hand, meaning a technician must sit and watch a replay of 24 hours of heartbeats. With a pulse of 60 beats per minute, this totals 86,400 beats while it goes to 100,800 beats at 70 beats per minute. This is a fair amount of data to carefully examine. Ordinarily, that is done by hand or scanning.

Another monitoring system that has found favor is used for patients located in a hospital coronary care unit (CCU) and also to those who are postoperative. Monitoring while in the CCU is self-explanatory. It provides instantaneous data to the medical staff for emergency help dependent on the telemetry signals and data from the patient. Monitoring in a postoperative mode during recovery typically involves daily or near daily attendance of the recovering patient to a hospital located exercise room. It is not uncommon for patients in this status to really want to change their lifestyle. Habits die hard! After not exercising for 20 or 30 years, after eating almost anything that they desired for the same time interval, and after accumulating excess weight, the patient then gets something of a scare. from the cardiovascular episode. Patients then immediately seek a new lifestyle that will fix up the accumulated problems and damages suffered in their body after 20 or 30 years of neglect. In a particular instance, they may go to an exercise facility maintained by the nearby hospital. In the exercise room, they typically will check in, be fitted with a frequency modulated (FM) telemetry system, and then will be instructed to exercise at a very gentle and slow pace on various machines under the watchful eye of medical personnel. The personnel not only watch the patient visually through a window, they also watch the FM telemetry signals received from the patient during the exercise session. Assuming that the patient is faithful to the program, they will build up some level of performance on the machines thereby strengthening their body and strengthening their heart in a post recovery mode. It is not uncommon for patients to continue this for many weeks always under the watchful eye of the attendant personnel when coupled with them via FM telemetry. However, there comes a day when the patients have to exert themselves away from the medical facility, away from the watchful eye of medical personnel who have by this time become very familiar with the patient's base line conditions and without the comfort of the telemetry system. Chores just as simple as mowing the lawn, shoveling snow from the sidewalk, or bringing in groceries can bean exertion of an unknown level, likely to cause a raised pulse, and possibly subject to stress as a result of the missing comfort provided by the FM telemetry and attendant medical personnel. That fear itself can add stress to the patient prompting even higher levels of pulse rate, shallow breathing, etc. All of these factors occur when the recovering patient forgets and undertakes a task or meets a challenge away from the safety of the controlled exercise routine. Another aspect of heart care is absence of noticeable pain. The pain in some people is minimal because there are fewer nerves in the heart region compared with the face or hands. Over time, cumulative small MI events may collectively damage the heart silently, i.e., with no alarm.

By contrast, it is most desirable that recovering patients be discharged to undertake a lifestyle which is substantially free of medical intervention. In attempts to rebuild strength, they are encouraged to undertake walking programs and other exercise regimens which build in difficulty over time. While the difficulty may build, the patient must have the courage to jump into that program knowing that controlled physical exercise is the best mode of recovery. That, however, is hard to do without medical supervision. That is difficult and a fearful thing in general terms. Monitoring of the data generated by a patient throughout the day in a post recovery mode is not possible because it would otherwise require t h e patient to simply live in the hospital or in the adjunct exercise facility. That is unwieldy and not reasonably calculated to restore the patient to "normal" living as defined by the life of that patient. The goal, it would seem, is to restore the patient to a normal job situation with normal exercise, but to increase and enhance the exercise level so that the patient can recover to the level he or she had before the episode and also to hopefully increase their strength by a new lifestyle featuring appropriate exercise. This can be seen only by observation of the patient over weeks, or preferably over many months, so that the patient can be restored to an effective status.

SUMMARY OF THE INVENTION

The present disclosure sets forth a monitoring system which is particularly effective for patients after discharge from a medical facility. This typically is applied to a patient after a myocardial infarction (MI), or after heart surgery of any sort. Alternatively, the monitoring system can be applied to elderly patients who, on a regular checkup, have been discovered to have a cardiovascular decline which requires some change either by medication but at least involving some level of exercise and other treatment. For instance, with a patient of 80 years of age, it might be appropriate to establish monitoring to look for measured data supportive of medical intervention by installing a pacemaker to change the heart rhythm. Another aspect may relate to surgery to correct valve action in the heart where the valve failure is episodic, and not otherwise chronic. In other aspects, the present monitoring system can be installed and used with a patient for several weeks or months to safely conduct the patient to the end of an exercise phase during recovery. In this instance, a distinction is made between exercise for rebuilding and exercise at a maintenance level. In the latter instance, the restored vigor of the patient often enables the patient to be discharged from a maintenance program. In other instances, it may be necessary to monitor that particular patient essentially for the remainder of their life.

As stated previously, the present disclosure also sets out a monitoring system which enables a patient to be monitored in a medical facility, typically including a CCU, and to be subsequently monitored upon being discharged to a regular room and then discharged from the hospital. Alternately, it can be applied to a patient who develops a long term trend indicative of a slow loss of vitality. In any instance, this equipment can be applied to obtain monitored data of the patient over an interval of time so that the patient can be observed while within, or more typically away from the medical facility. Because the test equipment worn on the person is omnipresent, it becomes a matter of second nature and will become less stressful than the conventional visit to the doctor's office. Moreover, this enables monitoring of the patient while out of sight.

One aspect of remote monitoring is the difficulty of collecting all of the data and then observing that data dynamically. In the ideal situation, this collection and observation process should not be done by human intervention. To be sure, well trained cardiologists can recognize nuances not otherwise visible. While this may be the best analytical tool available short of a catheter, it cannot be used except when limited to hospital circumstances. In other words, it is an important data point which can be input so that the patient thereafter can be monitored with a continuing observation yet without the crucial attendance required at the medical facility. The present disclosure sets forth a monitoring system which can sound alarm signals without human intervention. Alarm signals presently exist where the heart rate exceeds specified limits, i.e., it goes below 60 beats per second (BPS) or above 120 BPS. A more sophisticated analytical approach is obtained by the present monitor system. Further, the system of the present disclosure enables monitoring wherein the patients are able to go about their business to any number of places or facilities. They can roam far and wide. The monitor data are transmitted, by means of a transmission system, to a diagnostic system located at a home base. The amount of data transmitted is typically large, but can be compressed by means discussed in a subsequent section. As an example, a conventional spread of electrodes involves 12 electrode terminals attached to the body for a full spread of EKG signals. In effect, there is a base electrode for reference and 11 different electrodes connected elsewhere on the patient. The electrodes are connected at specific locations. The data can contain systematic errors such as drift and base line shifts. The data, however, when dynamically presented on a cathode ray tube (CRT) or strip paper chart recorder, before the cardiologist, is visually corrected for systematic error by the cardiologist based on experience. For instance, there are direct current (DC) offset errors that arise from lead connections. In a qualitative sense, the cardiologist can simply ignore that drift. The base line for a given signal will wander or drift. This is especially true during physical exertion by the patient. Some of these systematic errors derive from perspiration, movement, respiration, changes in skin condition, changes in internal electrolyte concentration, and the like. The EKG signal again can be corrected visually by the cardiologist in attendance simply by looking at that and knowing the exercise state. However, the intelligence to make this kind of transference is not so easily implemented unless the cardiologist is visually observing the patient.

There is another aspect that is significant in collection of a full spread of EKG data signals. The position of the heart within the body will impact the EKG measurements. This changes the response time lag between electrodes. In a real sense, it is fictional to represent the heart centered in the body. There are positional and displacement changes which occur from patient to patient and which can even occur in the same patient over time. The patient may gain or lose weight. The patient's posture and muscular strength may change. Then, from one patient to another, the heart will be relatively displaced. The displacement includes a radial component, i.e., from the heart at the presumed center of the body radially outwardly to the location of the electrodes positioned around the body of the patient around the thoracic cavity. All of these variations impact data reading. All these factors not only impact the data collected from a properly installed twelve electrode spread, but they also impact in ways that the cardiologist can accommodate when visually eyeing the patient but which cannot be easily dealt with without substantial foreknowledge.

One aspect of the displacement problem should be noted. From patient to patient, the heart as a signal source relatively rotates. From one extreme to the left or right in one patient to another, this rotation can be perhaps 40° or even 50°. Rotation left and right is possible between patients. Also, the heart can rotate upwardly or downwardly to present a different aspect. Viewing the heart as a signal source, the heart functions as a finite vector source in space. In general terms, this results from the fact that the input signal to the heart starts the heart beat as a muscle contraction which ripples over the surface of the beating heart. While it has a finite beginning point at an initial instant, the flexure of the heart during contraction ripples outwardly from that location, radiating over time in circular fashion. Distortions of the radiated ripple result from prior damage to the muscle. Suffice it to say, this kind of ripple effect on the surface of the heart (assumed to be spherical for easy discussion) results in a rotative shift of the heart from patient to patient. Again, the cardiologist examining the patient personally and observing the strip chart recording in person can make the mental adjustments or "normalizations" necessary to read the set of signal traces describing the patient's heart functions. While easily done in person, it is not so easily done in practice absent the hands on relationship between the cardiologist and patient.

The present disclosure sets out a system which enables a large amount of cardiovascular data to be gathered, and yet which also compresses that data and reduces the data flow rate to that permitted by conventional telephone lines, i.e., a pass band of about 4 KHz. Data compression and redundancy removal are important aspects of this feature of the invention. This involves the selection of desired signals which are different from patient to patient. More will be noted concerning that hereinafter. The present invention additionally enables monitoring of an important variable which is the oxygen content in the blood. The heart and lungs cooperate to refresh the oxygen level in the blood stream. This is a highly significant data to the well being of a recovering heart patient.

The present invention is summarized as a telemetry system which enables a patient to roam far and wide and yet to be continuously monitored at a remote station. The monitoring system utilizes a multiple lead EKG spread, preferably 12 terminals, on the patient. The output signals are provided to a signal conditioner and then to a multiplexer. The multiplexer is connected with an analog to digital converter. Preferably, the signals are digitally handled to reduce bias in the signals, to adjust the base lines of the signals, and then to perform a decomposition on the signals. The three foregoing steps are helpful to reduce signal bias as a result of skin changes, change in base line, base line drift and the like. The decomposition step is involved in mathematically rotating the measured data to take into account differences in heart position within the chest cavity. The signal is compressed, modulated and then transmitted. The patient also optionally carries a receiver with an alarm. The receiver is connected to a system adjustment circuit. That provides a number of override signals. At a remote station, the equipment includes a receiver, demodulator, decompressor and then inputs the signal to a neural network. The neural network processes the measured data and presents the processed data to a data recorder. An alarm device is connected to offer it on a screen of a CRT. This enables human intervention. The human intervention can then operate a transmitter to signal an ambulance or hospital in the event of an observed, critical abnormality of the measured or processed data. An alarm can be sent back to the patient. The remote equipment utilizes a receiver, demodulator, decompressor and neural network which is input with selected presets, patient data and learning data so that the measured cardiovascular signals can be dynamically processed. This enables a cardiologist on duty at a central location to handle literally hundreds or thousands of patients, and to intercept data from each and every one of them, and to make a quick diagnosis based on their actual history and present needs. It also enables transmitting a signal for instance to a hospital or ambulance to alert for an incoming situation and to also transmit a signal to the patient.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

The present disclosure is directed to a health monitoring system having special application to cardiac patients. It should be understood that the system can be modified to monitor patients suffering from other symptoms or diseases 'such as diabetes, high blood pressure, hypertension, pregnancy, epilepsy and the like. Beyond that, it also is a monitoring system able to watch over and alarm or alert rapid medical intervention should the need arise and get help for the patient.

Figure 1:
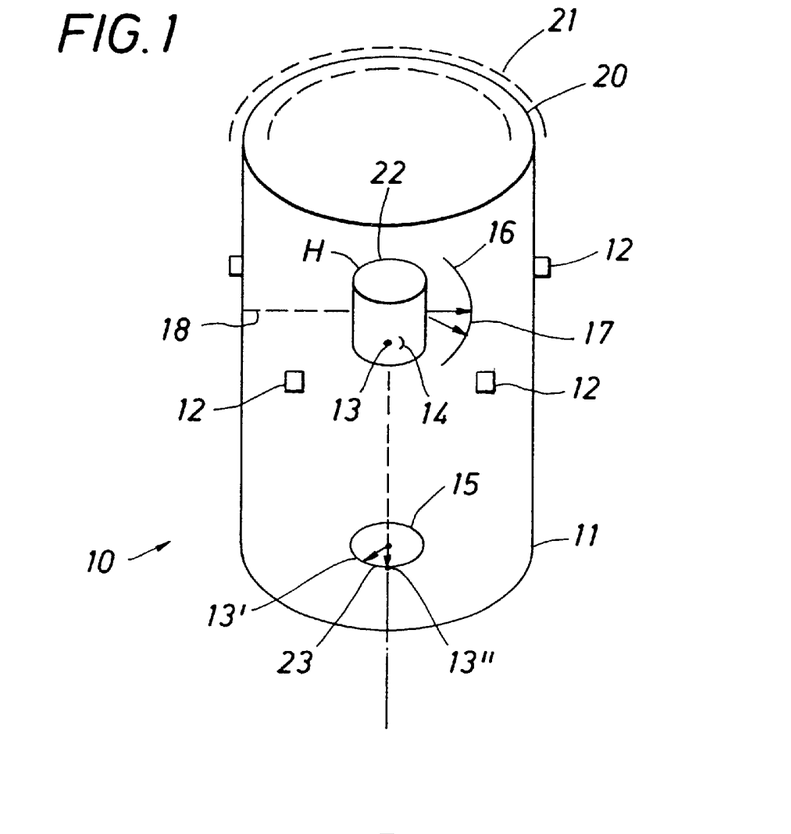
FIG. 1 is an functional representation of the geometric location of the heart within a body, with respect to a reference location.

To set up part of the problem involved in this type monitoring, attention is directed to FIG. 1 of the drawings where a geometric representation of a body of a patient is illustrated. This representation is tutorial. The patient is represented in symbolic form at 10. The trunk of the body is illustrated at It as comprising an elongated cylindrical member. This is idealized for tutorial purposes. The number 12 identifies several electrodes which are attached around the trunk 11 of the body 10. Some of the electrodes 12 are placed on extremities including arms or legs as desired. The several electrodes 12 shown in FIG. 1 help make clear the manner and mode in which signals are detected. The trunk 11 of the body 10, having the form of an idealized right cylinder, mounts the electrodes 12 at spaced distances from a heart H in the interior of the body 10. Again, for purposes of geometric positioning, the heart is represented as a right cylinder 22. In actuality, it is not at all shaped like a cylinder, but it is more of a round sphere about the size of a softball. It is however easier to represent certain of the problems that arise with the heart position in the trunk of the patient's body utilizing the right cylinder 22 at H. The numeral 13 identifies a selected location on the heart at which a signal triggering a heart beat is initially observed. The signal is located at a specific point on the heart. It propagates outwardly in a radius of curvature represented at 14 in FIG. 1. The radius of curvature grows until the signal propagates over the surface of a substantial region of the heart. In one sense, the heart serves as a signal generator which forms a signal at a specified sequence. The right cylinder 22 representing the heart H is projected down onto a circular profile 15. The corresponding projection of the point 13 is on the forward point of that circle at a forward location. Assume for purposes of arbitrary description that this projected point, identified by the number 13", is precisely centerline of the chest of the patient and is pointed directly forward. In that sense, the point 13" is located at that location which will be described as the zero reference point. This dimensional description is only a portion of the descriptive data locating the heart. More will be added later. The electrical axis of the heart H can be mislocated so that the projection of the point 13 is located at 13'. The included angle 23 between 13' and 13" can be as much as 40° or so. In other words 13' can be offset as much as 20° to the right or left from patient to patient. This describes a total included angle of about 40°. Even 50 may be noted in some situations.

FIG. 1 further includes a projection to the side of the heart along the arcuate line 16. Here it will be noted that the side profile of the heart can show, and does show, that it may be canted with rotation to the right or left. The included angle 17 can also range as much as several degrees above or below the horizon which is drawn through the heart as a reference. The total variation of the angle 17 is upwards of about 40°. As will be understood, the actual location of the heart with respect to both of these measurements can be expressed in the sum of the two angular measurements 17 and 23 which represent the resolved orthogonal variation. The departure from the reference points can aggregate as much as 40° or 50°. In other words, the heart may be rotated to the right or left (clockwise or counter clockwise) and tilted up or down.

FIG. 1 shows the heart H represented by the right cylinder 22 on the centerline axis of the thoracic cavity of the body 10. It is assumed to be located on the centerline axis. There is a lateral distance to the wall of the body 10 indicated at 18. This distance should nearly be the same to the left or right of the heart H, and the distance to the front and back should be substantially the same for both. In actual circumstances, it is not always the case. Thus, the heart is subjected to angular displacements measured by the angles 17 and 22, and to lateral displacement measured by the dimension 18. Both are equally problematic in data collection and interpretation.

The heart in the patient shown in FIG. 1 is subject to another source of error. The thoracic cavity defines the location of the several electrodes 12 attached. The electrodes 12 are placed on the skin, not under the skin. The idealized thoracic cavity has a radius represented at 20, this being a solid line. In reality, the actual radius may be given at 21 where is either greater or less than 20. Again this will vary from patient to patient, and over time will vary with one patient. The patient may grow larger, gain weight or eventually lose weight. The shape may be distorted by other conditions such as the cumulative wear of bad posture, or other skeletal distortions. There is always a change in the shape for women patients during pregnancy. The diaphragm will typically move and reposition the heart and other components in the thoracic cavity. Thus, the thoracic cavity diameter idealized at 20 may change significantly. At least, the diameter varies from patient to patient.

The foregoing sets out a number of geometric induced, systematic problems that are encountered in reading EKG data. When the cardiologist is present and able to read the data in a strip chart recorder or on a CRT monitor while looking at the patient, and comparative readings are made from trace to trace, the medical specialist trained in reading that sort of data can make, on the spot, mental adjustments which take out problems resultant from distortions of this sort. If nothing else, the specialist has the option of repositioning a few, or perhaps several, of the electrodes to get a dynamically corrected data. As will be understood, this can be done in a number of ways. The present invention, however, digitally processes the data so that the artifacts resulting from geometric variations in heart placement, angle of presentation and thickness of the body are removed and the heart is moved mathematically to an idealized, or "reference" location. More will be said about this below.

Figure 2:
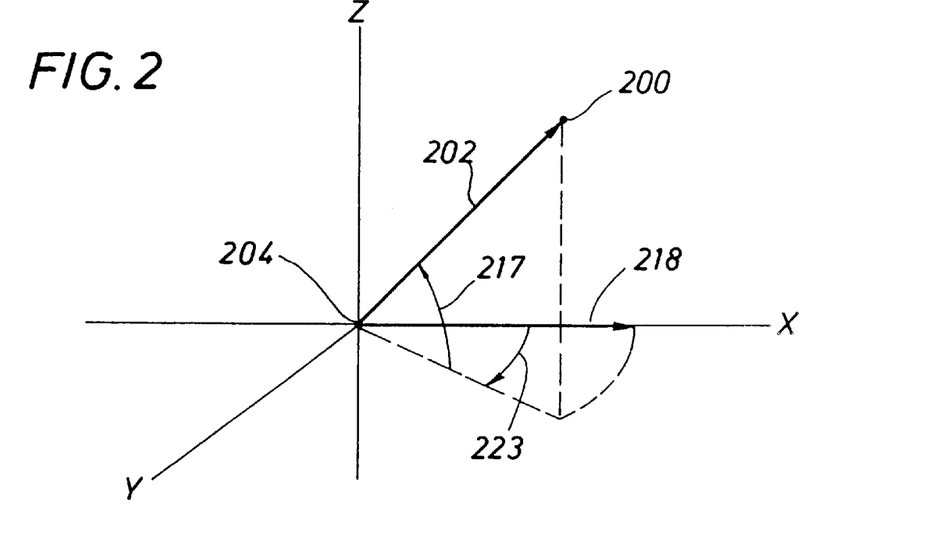
FIG. 2 is a vectoral representation of the location of the heart within the body in Cartesian coordinates.

FIG. 2 is a vectoral representation of the heart with respect to a "standard" or "reference" position as discussed previously in the geometric tutorial. The position 200 of the heart is represented by a vector 202 with its origin at a reference position 204. This is useful in representing the heart beat, or signal source. Recalling the discussion of FIG. 1, The vector 202 is the sum of horizontal and vertical rotations, and horizontal displacement. More specifically, angle 223 represents the rotation of the heart in the horizontal (x-y) plane (see angle 23 in FIG. 1). Angle 217 represents the rotation of the heart in the vertical (z) direction (see angle 17 in FIG. 1). The displacement 218 represents the lateral displacement of the heart in the thoracic cavity (see dimension 18 in FIG. 1). The position 200 of the heart is, therefore, defined in three dimensional space by the vector 202 with its origin at the reference point 204.

Figure 3:
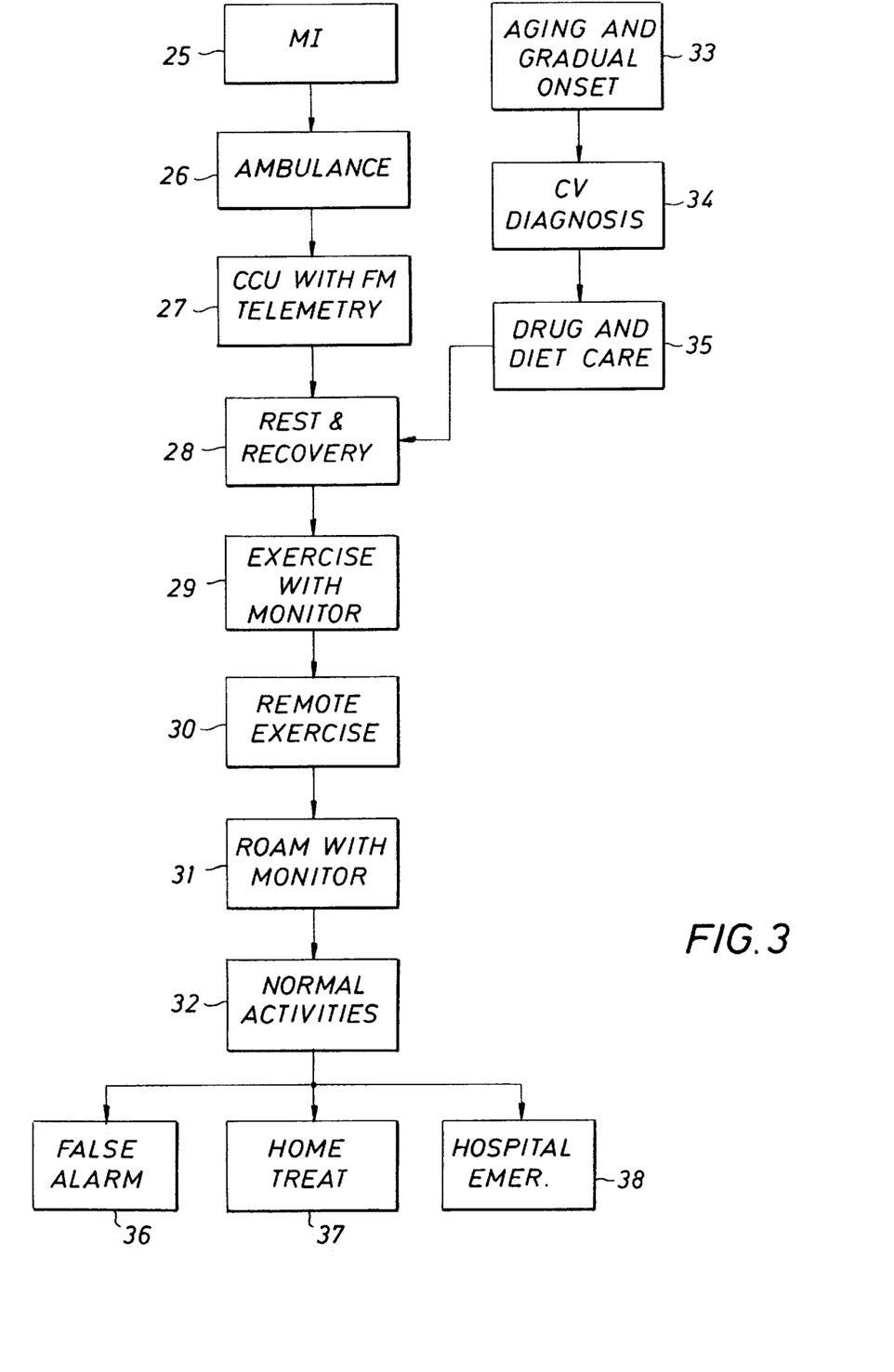
FIG. 3 shows a block diagram schematic of an improved method of treatment of heart patients.

FIG. 3 shows a block diagram schematic of an improved method of treatment for heart patients having a wide range of difficulties. Two different problems are dealt with in FIG. 3. The first involves the sudden onset of heart difficulties, typically chest pain and ultimately involving a heart attack otherwise known as myocardial infarction (MI). The MI occurs at 25. Typically, the patient is moved by ambulance to a medical facility. This is step 26. At the medical facility, the patient is normally placed in a coronary care unit (CCU) where the patient is kept on hard wired or FM telemetry connected leads. This step 27 lasts a few days or until the patient is stabilized. Suitable heart monitor medications are administered along with blood thinners and the like. After a few days, the patient will be discharged from the CCU to a regular room and then to home care. In the interval when the patient is in CCU and sometimes when the patient is in a convention room but prior to discharge, they will be watched from the nursing station through FM telemetry but they will ultimately be disconnected from that and sent home. The next step 28 represents that recovery step where the prescription may include medication, but it also at least includes some rest and recovery. After a short interval, the patient will then be requested to report to an exercise room or other facility at the medical or other facility. Here, the patient will be put on a controlled exercise program beginning with very low levels of physical activity. The patient is monitored during this. The step 29 shows that monitoring continues throughout the exercise session. If the exercise session lasts 20 minutes to start, the cool down session may last another 30 minutes so that the patient is observed visually and typically by some form of telemetry. Vital signs may be taken before, during and after the exercise session. This session will be repeated several times a week, for instance four or five times per week. While beginning very gently, the exercise level will be raised and the performances required of the patient will be raised. This performance continues on as the patient continues to exercise with both visual and telemetry monitoring schemes.

Finally, the patient is graduated to a remote exercise routine. The step 30 shows the remote exercise sequence which is added. For instance, the patient may be discharged with instructions to walk two miles per day for five days per week in an interval of 30 minutes each time. The patient will be instructed to walk on level ground. Having done the equal to that in the exercise facility and especially connected with a monitor set forth in this disclosure, the patient will then have the confidence that they are not doing anything excessive or foolish risk a relapse. Moreover, the patient can then go forward with this remote exercise routine 30 away from the watchful eye of the medical personnel. The present invention, however, proposes to modify the step 30. Not only is the exercise carried out in a remote fashion such as walking two miles per day, the patient can do this while equipped with the apparatus of this invention which will be discussed in detail with regard to FIG. 4. Now, the patient is therefore able to be remote from the medical facility and exercise where it is most convenient to the patient. During this stage of the patient's recovery, they realize that repeated trips to the medical exercise facility is a heavy burden. They would rather exercise outdoors or in familiar neighborhoods. For a multitude of goods reasons, patient recovery seems to be better in a more normal setting away from the exercise facility. Perhaps the patient is encouraged by returning to normal circumstances of life. If nothing else, the patient is not faced with making the trip to attend to the exercise session. Also, it is also important that the patient go about the remote exercise routine repetitively to build up their confidence in their body and to rebuild the assurance that they are not subject to a momentary relapse.

Again referring to FIG. 3, the procedure of the present disclosure includes the step 31 which involves patient roaming subject to the monitor. Here, the patient can go about a variety of duties. The geographic area for the roaming at step 31 is the area where the patient normally travels both for home activities and work activities. It includes stores and other businesses such as the post office. It can include trips to see friends and family. The roaming is carried out in the immediate vicinity so that the patient knows that, if an unexpected pain occurs, they can quickly return to the hospital or other health facility where they first received care. This time, however, they likely will be able to readmit themselves without an ambulance ride because they will be more alert provided they have stayed with the exercise routine. The step 32 shows the patient going about activities which are normal for that particular patient at that stage in life. They can do outside activities around the house and carry on normal activities with a minimum of intrusion as a result of the monitoring of the present invention. These steps, however, are deemed to be normal activities except that they are carried out subject to monitoring. Details of that will be given below.

In some instances, this procedure is implemented from other medical contacts. While the patient may not be struck down suddenly with MI hence requiring a ride to the hospital in an ambulance, the patient may nevertheless detect over a period of time that some thing is not quite going right. FIG. 3 shows an alternate step at 33 where aging or other gradual onset symptoms manifest, thereby prompting the patient to seek the assistance of a cardiologist or other health care professional. The symptom may be angina (pain) or sensation of an irregular heart beat. A cardiovascular diagnosis is made at step 34. This often will be done in the office or perhaps in a nursing home where the patient has continued to live, living well beyond the retirement age and up into the 70's or 80's years of age. If the patient does not have the sudden MI indicated at 25, the patient then can undertake some treatment at step 35 under control of the treating physician after the appropriate cardiovascular diagnosis and this treatment is undertaken typically with drug and diet care. After that has been established as a solid regimen for the patient, the patient will then be instructed to undertake the appropriate rest and recovery step 28 previously described. Thereafter, the patient may be instructed in the same sequence of steps 29 through 32 previously described. As will be understood, a person can enter either sequence depending on the condition of their health. The last three steps of FIG. 3 are discussed below.

Figure 4A:
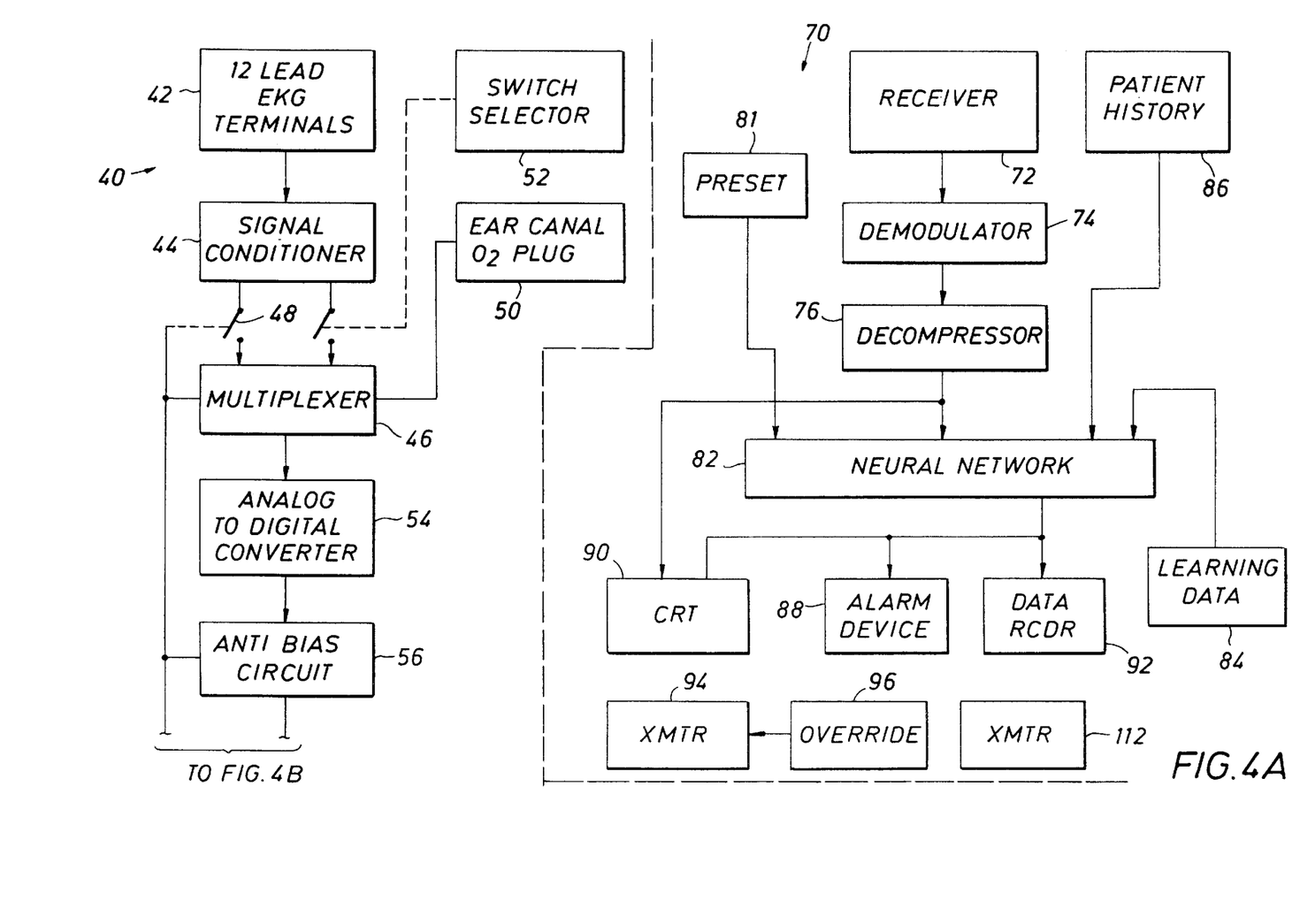
FIG. 4 is a schematic block diagram of apparatus and methods of the present monitoring system.
Figure 4B:
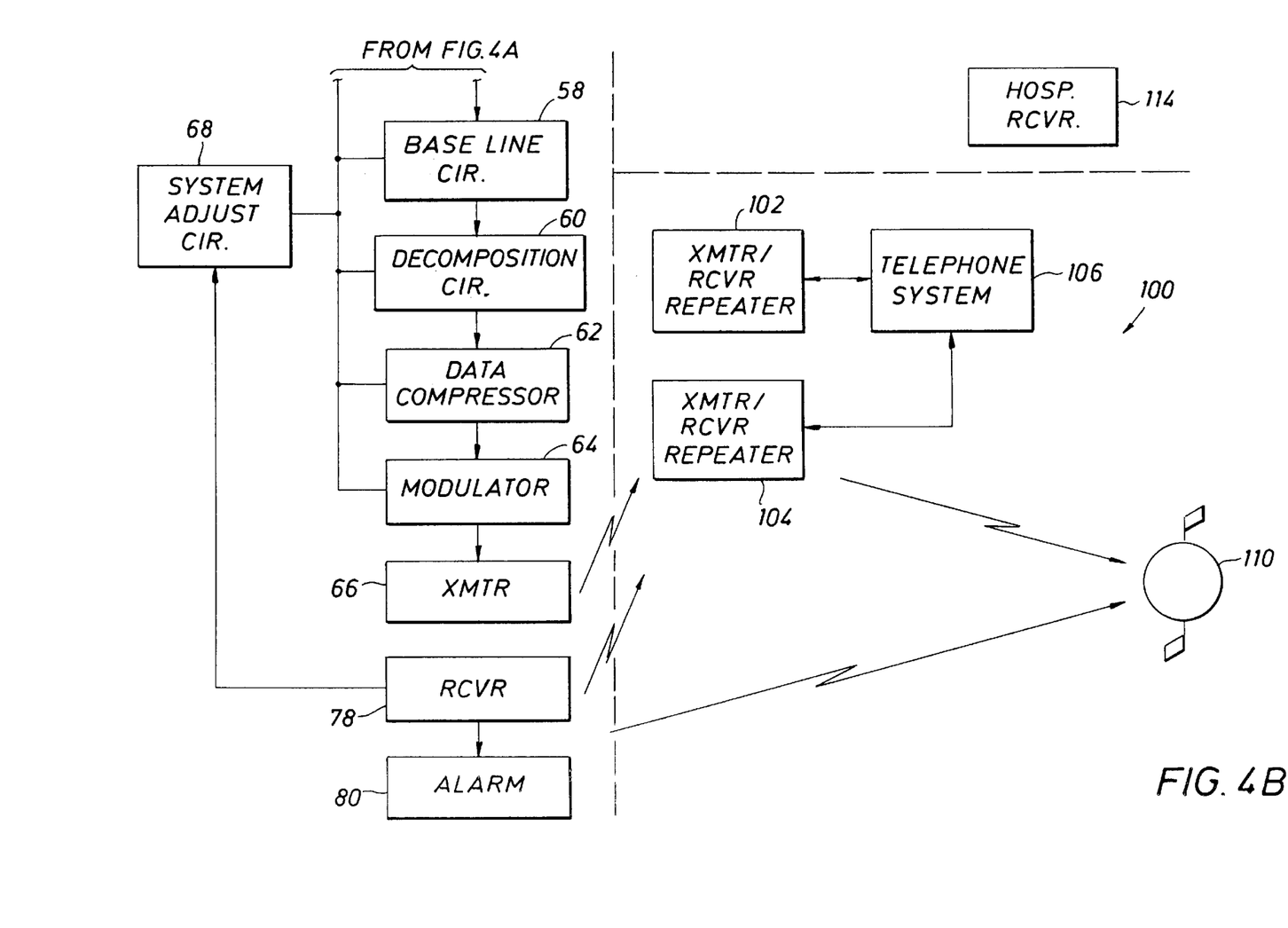

Attention is now directed to FIG. 4 which sets out the apparatus of the present disclosure. Major elements of the apparatus consists of an patient portable system and a central coronary response system. These elements enable the steps shown in FIG. 3 to be carried out.

PATIENT PORTABLE SYSTEM

The equipment worn on the person is on the left side of FIG. 4 and is indicated generally by the numeral 40. This equipment can be worn as a portable device. It is not very large and can be worn at or on the person. It has a size enabling the device to be slipped into a pocket and hidden safely out of the way or attached elsewhere on the body.

In FIG. 4, the patient mounted monitor system 40 incorporates a set of EKG electrode terminals 42. In the preferred form, twelve electrodes are installed, although that number may be reduced later as will be defined. Twelve electrodes are used to collect a full set of cardiovascular related signals.

The signals are output from the twelve EKG terminals. The twelve electrodes are connected to individual signal conditioning circuits 44. These provide an appropriate impedance match, and input the signals for subsequent processing. Some and preferably all of the twelve leads are connected through a multiplexer 46. The multiplexer has an input provided through a set of switches 48 so that different leads are switched on and off. More will be noted regarding that below. The patient can provide additional data and one such data is the measure of oxygen in the blood. An ear canal $O_2$ plug 50 is mounted on the patient to detect the amount of oxygen in the blood. Ear canal detectors respond to a change in blood color and thereby provide an indication of the quantity of oxygen. Explaining briefly, the oxygen concentration in the blood is defined as 100% for the maximum value, with additional bands defined above 60, 70, 80 and 90%. In general terms, a healthy robust active patient will have a measure of oxygen of 90% or greater. A patient in the range of 60 to 70% defines the fourth band. Measures below this band are generally associated with death. Effectively, this defines four bands. The topmost can be represented easily by a two bit binary signal such as 00. The next band which is in the range of 80 to 90% can be represented as 01, and other bands are added to that definition. This provides relatively easily measured data which is important to the health and well being of the patient.

Continuing with FIG. 4, as noted the EKG terminals normally provide twelve data pads and they are connected to the switches 48. A switch selector 52 is included with the patient to enable or disable selected ones of these electrodes. More will be noted regarding the number of electrodes involved in a sequence of operation. Assume for the moment however that all twelve signal pads are open from the signal conditioner 44 to the multiplexer 46 The multiplexer 46 provides an output to an analog to digital converter (ADC) 54. The ADC changes the analog signals into sampled digital words. The sampling rate interleaving is controlled so that the data output is sufficient while avoiding a high level of redundancy. Consider as an example oxygen level in the blood from the sensor 50. Generally, that data changes slowly (except it is more dynamic in some emergency events) and is measured periodically. The measured value is input through the multiplexer and then is converted into a digital word. There are four measured values permitted in the example just given. That binary data is relatively easily handled and does not need the ADC processing that is required for the heart beat monitoring. A bias correction circuit 56 is included. There is the risk of measurement bias as discussed previously. Signals are defined between two of the electrodes. There is always the risk of a deviation or drift dependent on the nature of the skin. Skin conditions vary significantly. It is desirable that all the signals have about the same scale factor but this is sometimes somewhat difficult because the skin on the same person can be quite different. Offset errors are substantial for those terminals 12 affixed to the chest cavity. These biases can sometime be eliminated, at least initially, at the time the electrodes are installed. In effect, a signal from one of the leads is observed over a time interval much longer than the period of the variable being measured. This yields a "moving" average of the typically periodic variable being measured. A slowly varying change in the average is indicative of a bias change. This "average" measurement is then subtracted from the measure of the periodic signal to reduce bias effects. The bias can arise as mentioned from a variety of skin conditions. Skin can vary depending on the location of the skin on the body (the skin is much tougher in the palm compared to the earlobe). The skin can vary with dermatology of the patient, and can vary dependent on race, and exposure to outdoor climate. There are many other factors which impact the skin including the propensity of the patient to sweat, electrolytes of the patient and many other factors. Suffice it to say, DC offset as a result of skin contact at the terminals has to be dealt with. While that can be done readily with visual observation, it is somewhat more difficult to do by a health care professional dealing with transmitted data. The anti bias circuit 56 essentially "corrects" the transmitted data for slowly varying bias changes after electrode installation on the patient.

The electrodes are subject to errors in addition to the DC offset just mentioned. The base line value will wander or drift. Such fluctuations are typically relatively slowly varying in time, and are induced by changes in patient perspiration, patient movement and respiration. Base line drift can produce misleading ST displacement in the EKG. ST distortion can lead to false diagnosis of ischemia. This must be removed. It is desirable to accomplish this in a digital fashion so that a digital filter can remove the base line drift. The target for this is to implement a filter which has a magnitude response which is flat in the pass band and which possesses a sharp drop off on the flanks of the pass band to maximize suppression of typically slowly varying base line drift, with reduced or no displacement of the ST segment as a result of drift. A relatively low frequency source of baseline drift, i.e., 0.4 Hz, can be removed for base line integrity. The base line drift according to the described filter is successfully removed. This is accomplished in the circuit 58 shown in FIG. 4.

Recalling FIG. 1 which shows the position of the heart in the chest cavity, it is subject to variation in position. There is a horizontal angular disorientation in one dimension, tilt or rotation in another dimension as represented by the curvature 16, and lateral offset represented by the radial distance 18. The orientation is illustrated vectorially in FIG. 2 in Cartesian coordinates. As also noted, the chest dimensions can vary at 20. Heart position within the chest cavity of varying dimensions as described with these four variables can impact the EKG signal measurements and produce error in interpretation. It is desirable to decompose the EKG signal into orthogonal components in the time domain rather than rely on corrections based the spatial orientation of the current source on the heart, which are difficult to determine. Recall that the periodic EKG signal of interest begins at a point 13 and propagates outwardly. Unprocessed data measured by each electrode will, therefore, exhibit maxima and minima in the time domain. The occurrence in time of a "peak" representing a cardiac function as measured by one electrode will typically be displaced, in time, from peaks representing the same cardiac function as measured by other electrodes. This displacement will be a function of electrode placements, and the orientation of the heart. If electrodes are placed in "standard" locations of the patients, then signal displacements in the time domain for a "standard" heart orientation will be known. Any observed perturbations in displacements are, therefore, attributable to "non standard" heart orientation. These perturbations are quantified and used to correct each electrode signal for orientation perturbations. The change from the spatial domain (as illustrated in FIGS. 1 and 2) to the time domain in orthogonal coordinates adjusts the signal wave form measured by each electrode to present the data in a different aspect. This processing, in effect, rotates the heart to a desired centerline "standard" position at a fixed distance. This brings the EKG data to a common source and thereby fixes the criteria for measurement, observation, and interpretation. This decomposition step at 60 treats all the data from the multiple electrode leads as a group and normalizes the data to a standard geometry for interpretation. In non-mathematical terms, the heart as observed by the twelve leads is rotated to that the signals are orthogonal, and not subject to position distortion as previously described.

The decomposed signal from the circuit 60 is sent to a data compressor 62. Redundancy is reduced by the circuit passing only significant changes in the measured wave form data rather than the entire wave form, or by simply reducing the number of transmitted wave forms as will be discussed in a subsequent section. The signal is then provided to a modulator 64 and that is output to a transmitter 66. The transmitter 66 sends a meaningful signal elsewhere. Significant benefits are noted with this transmission elsewhere as will be explained.

CENTRAL CORONARY RESPONSE SYSTEM

Again referring to FIG. 4, the numeral 70 identifies a central response system located away from the patient who wears the apparatus 40. The central response system 70 is located at a medical institution which, for instance, has a full time cardiologist on duty day and night. It could be located in a large metropolitan area so that it can provide monitoring services to any number of patients. Presumably, things will go smoothly for any particular patient on any particular day; nevertheless, with hundreds or perhaps thousands of patients undergoing monitoring, the emergency attendants at the central facility are on duty. Cardiologists tremendously assist in providing medical intervention. Just as importantly, the system 70 is a device which will be described with "unmanned" operation which continues to monitor the patient wearing the equipment 40. In this aspect, it works day and night and will not be interrupted should trained personnel not be physically present. The equipment 70 includes the receiver 72 which is tuned to the frequency of the transmitter 66. This transmitted signal at the receiver 72 is one of many. The segregation of individual transmitter signals will be discussed below. The receiver 72 outputs the received signal to a demodulator 74 which then provides the signal to a decompressor 76. So to speak, these recover the signal and restore it to a condition which represents the output of the twelve lead terminals placed on the body of the patient. It is, however, modified in several important aspects which should now be noted. The transmitted and recovered EKG signal at the receiver had been shifted. The shift takes into account variations in position for the patient as presented in the discussion of the decomposition system 60, and with regard to FIGS. 1 and 2. Tilt and rotation of the heart with respect to the chest cavity is reversed. Not only that, the heart spacing to the side wall of the cavity is corrected. Further, the signal from the large spread of leads is reduced in terms of redundancy with the circuit 62. Explaining, there are twelve leads in a typical spread of electrodes to conduct an EKG test. Usually, events occurring in the heart are periodically reproduced at several different electrodes. They may show different aspects of the same event but the different electrodes provide that signal from a different perspective and therefore the data from the twelve leads includes a significant amount of redundancy. Once the patient has been placed under medical care, the nature of the ailment and the anticipated wave form indicative of difficulties will be predictive so that the number of leads can be reduced. While twelve electrodes are required at an initial condition, the number of active leads for monitoring can often be reduced to a lesser number. Consider for instance a patient who is subject to an irregular heart beat. That signal in the ECG wave form is readily understood and recognized. With the history of the patient, the number of specific EKG leads can be reduced perhaps to four. This is implemented in the patient mounted equipment 40. Returning now to FIG. 4, the switches 48 are interposed between the twelve EKG terminals and the modulator 46. Several of the switches 48 can be opened. A switch selected 52 is provided for that. Assume for the moment that the patient is equipped with twelve leads. The switch selector 52 is set to open a selected number of these signals thereby interrupting those signals because they are not needed. In effect, redundancy is reduced. The switches 48 are also subject to control of a system adjust circuit 68. The circuit 68 is provided with a received signal from the receiver 78 in conjunction with an alarm 80. The system adjust circuit is provided with digital word instructions which are decoded by it to change the switches 48 to drop one or two of the terminals so that redundancy is reduced and yet the crucial signal for the care of that particular patient is nevertheless processed through the multiplexer and other components for transmission. Thus, the twelve leads may be placed on the patient at the time of discharge from a medical facility, the switch selector 52 is then operated to reduce the twelve to a steady state operation for maintenance with six of the signals provided, and then in the event of difficulties, the system adjust circuit 68 is operated to change the status of the switches 48 thereby receiving data from ten of the EKG leads. Or, perhaps only three leads are sufficient to send the needed data for that patient.

Again referring to FIG. 4, the receiver 78 is keyed to receive an encoded message. The encoded message carries with it the identification of the particular patient 40. The patient wearing the equipment 40 may have difficulties without even knowing that difficulties have arisen. For instance, an alarm condition may exist requiring the patient to quickly go to a medical facility. The alarm 80 is included for that purpose. Otherwise, continuing adjustment of the operation of the equipment 40 can be provided. The switches 48 can be toggled, and the operation of the multiplexer 46 can be changed also. In like fashion, the bias removal circuit 56 and the base line adjustment circuit 58 can be modified or altered. Other aspects of the system including the decomposition circuit, data compressor and modulator can be remotely controlled as desired.

Going back to the central medical facility, the decompressor 76 provides the recovered unique signals from the patient to a neural network 82. The neural network is provided with a set of learning data from a data source 84. The particular patient wearing the equipment is tested several times, typically before the equipment is installed and that is represented as patient history which is input at 86. The neural network 82 is provided with appropriate presets 81 also. The significant aspect of this is the neural network operation. A neural network is defined as a system processing device typically having the preferred form of a software package which processes data. The teaching data is input so that the neural network learns and thereby reaches the right or correct decisions. A neural network typically has a first set of input terminals and a connected set of output terminals. In between, there are one, two or three layers of decision making nodes. The number of layers of nodes can be varied and the precise number of nodes in each layer can also be varied. A neural network is then provided with a set of learning data. This is used to teach the system. As an example, data from patients having a healthy EKG signal is input. Of necessity, there will be a range of data which still nevertheless represent the EKG signals of healthy patients.

The neural network is also provided with EKG signals from patients having difficulties. This enables it to learn how to recognizes the medical problems. Mitral valve relapse is an example. That data can be input and stored so that the neural network will recognize that problem when it repeats. The neural network thus detects and classifies any patient arrhythmia. Preferably, the neural network 82 is trained with a data base indicative of several types of arrhythmia which is furnished by the American Heart Association (AHA). So to speak, the irregularities indicative of arrhythmia for a given input data for one patient prompts the neural network to recognize the error (meaning the departure from normal) and to propagate that to the different levels of the neural network. Typical classified disease categories include several types of biventricular hypertrophy, many types of myocardial infarction and other disturbances to heart rhythm and signal propagation in the heart.

Through the use of the teaching data from the AHA, various types of heart irregularities signaled by the departure from the standard EKG profile provide an alarm condition interpreted by the neural network 82, Interestingly, the equipment at 70 of FIG. 4 responds to the neural network 82 by forming an output signal on an alarm device 88. At that time, the signal from the particular patient prompting the alarm condition is displayed on a cathode ray tube (CRT) 90 for skilled personnel observation. Here, the cardiologist optionally can come into play by looking over the particular reconstructed EKG signal prompting the alarm. The data are also input to a data recording 92. It is stored and later transferred to memory 86 storing the patient data where it will become a part of that patient's medical history. As part of the system, either automatically upon the sounding the alarm 88 or upon specific approval by the intervening cardiologist, a transmitter is operated. A transmitter 94 sends a signal back to the receiver 78 on the patient. Several things can be accomplished with this signal dependent on the instructions input to the transmitter 94. The cardiologist is provided with an override keyboard 96 so that a particular transmitted signal can be provided directly to the cardiologist to the transmitter 94. The keyboard 96 enables override signals to be created. These signals also are used to change the mode of operation of the patient mounted equipment 40. For instance, the redundancy can be changed completely by resetting the switches 48. More data can be input so that the cardiologist can require transmission of signals from all the leads on the patient. Assuming that twelve are present, all twelve can be operated. The switches 48 are reset to accomplish this. Adjustments also can b e made in the bias circuit 56 and the base lines of the signals can be changed by the circuit 58. All this can be controlled remotely. These changes can get carried out without alarming the patient because the patient does not necessarily sense, feel or know that changes are being made to equipment so that more detailed monitoring is then being obtained. On the other hand, the cardiologist can send or not send an alarm condition to the receiver 78 for sounding the alarm 80 to the patient. If that is done, it typically will involve instructions to proceed to a specified medical facility.

Certain aspects of data transmission between the patient mounted system 40 and the remote system 70 should be noted. They can be a few hundred yards or many miles apart. However, so the patient can undertake normal living activities, the patient typically is discharged from the hospital and the equipment 70 is operated from the facility to monitor the patient. The distance may vary quite widely. The equipment 70 can be located at the geographic center of a large population for easy monitoring. If need be, they can be connected together through a telephone system 106 which in turn takes care of the long distance transmission. The telephone system 106 can be connected also to the receiver 72 if desired. The communication equipment 100 also includes an optional synchronous satellite 110 equipped with a transmitter and receiver combination so that it also operates as a repeater. In that sense, it functions in the same way as does a satellite pager system. The signal can be transmitted from the patient 40 up to the satellite 110 and from there transmitted down to one of the repeater stations or directly to the receiver 72. The equipment 70 thus can communicate directly to the patient mounted equipment 40 or can take advantage of the repeater system. The current invention will utilize existing wireless and wirelan technologies as meadia of transmission.

One added link that may be helpful is to provide the intervening cardiologist with a transmitter 112 which transmits directly to the emergency room of a hospital. A receiver 114 within the emergency room is tuned to the transmitter 112. Automatically or by intervention of the cardiologist, the patient can be sent a signal instructing the patient to report immediately to a staffed hospital emergency room having appropriate cardiology assistance. The patient who is experiencing chest pains may want to go to the nearest hospital. However, that hospital will not know that they are coming. Moreover, they may or may not have readily available medical assistance and facilities so that emergency treatment might be delayed. Therefore, the equipment either automatically or through the intervention of the cardiologist sends through the transmitted signal to the patient support equipment 40 an instruction noted at the receiver 78 and which provides an output on alarm 80 instructing the patient to go to a particular treatment facility. It may not be the closest, but in terms of health, the instruction may tell the patient to pass by an overcrowded emergency room and go to a facility where help is ready to meet the patient literally at the front door and to undertake treatment immediately. Through this approach, the patient is sent to the correct location. Moreover, with the intervention of a cardiologist, or automatically through the operation of the neural network 82, the transmitter 112 is provided with an input indicative of the nature of the problem. That is transmitted from the transmitter 112 to the hospital receiver 114. The coded message will identify the patient, the instructions given to the patient, and tell the hospital through the receiver 114 that the arriving patient is having a specific problem as indicated by the EKG. Several options can then be executed.

Going back to FIGS. 3 and 4, it was noted that the patient is permitted to roam subject to the monitor and undertake normal activities at the step 32. In the event the patient perceives difficulties, the patient has an instant feedback system whereby the alarm device 80 provides instructions to the patient. Great peace of mind can be achieved if there is a pain, followed by that uncertainty in the patient and yet the equipment 40 operates successfully, transmits a signal and receives a signal back that the pain is not a significant event. In effect, the pain becomes a false alarm 36 and the patient is provided with a signal indicating to the patient that nothing need be done. While that decision might be made by the patient acting alone, when made with the assistance of this remotely located equipment and testing competency of the sort described in this disclosure, the patient has a distinct advantage when receiving the false alarm signal 36 indicated in FIG. 3. This, however, is instructed to the patient in an affirmative way. It is a signal saying far more than simply do nothing. Rather, it is a signal instructing the patient that doing nothing has been evaluated and is the wise decision.

Separately, medicines literally in the pocket of the patient comprise immediate treatment undertaken wherever the patient is located. That is indicated at 37 in FIG. 3 as the home treatment. The home treatment may be as simple as taking by mouth the typical nitro dose which reduces heart pain quickly. The third option is transmission of an instruction 38 to the patient to go quickly to a specific hospital emergency room entrance. This protocol may be required as a result of EKG data analysis.

Going back to FIG. 4 of the drawings, it will be noted that the patient mounted apparatus 40 stays in two way communication with the central medical facility 70, which is typically remote from the hospital containing the receiver 114. The neural network 82 provides the interpreted EKG data and significance of that data. The alarm condition indicative of medial difficulties is transmitted automatically, but is subject also to review by a n attendant cardiologist if desired. This intervention can materially shorten diagnostic times in emergency conditions so that patient treatment has started sooner and precious time is not lost.

The quick response of the present system is noteworthy. In real time, emergency medical conditions are signaled. This can start real time medical intervention. The patient may have only a short interval in which to deal with emergency conditions. One example of this is clot formation in the heart which event is signaled from the patient. Once the clot is identified, it may be appropriate to send a signal to the patient to intervene quickly by the administration of medications which dissolve clots. Such medications are most effective if administered within the first few minutes after the clot has formed. It is common that efficacy of these medications is seriously degraded if intervention is delayed by more than about 120 minutes. Clot dissolving medications are most efficient when quickly administered.

The data processing aspects of the present disclosure are limited by the data transfer rates entailed in the system. It is desirable that the multiplexer 46 be operated at a rate of about 3–5 times faster than the highest frequency component desired from the EKG signal. The Nyquist criteria in connection with the AHA definitions require sampling at least at a minimum rate just given. This sampling rate dictates the amount of data output from the spread of electrodes. In turn, the system provides the appropriately modulated RF transmission. That delivers a very large amount of data, i.e., the data transfer rate is quite high. The data transfer rate in perfect conditions might exceed about 50 kiloHertz (kHz). However, data transfer rates of this sort cannot be handled without some reduction in the data by reducing redundancy, etc. Probably the most limiting connective link reducing data content is transmission over conventional telephone lines. They are typically limited to about 4 kHz. Taking this constraint into account, the data compression scheme and the reduction of redundancy in the patient generated signal preferably provides a transmitted signal with this data content. In other words, the modulating signal encodes the signal so that it will pass through a telephone system.

The equipment 40 on the patient is preferably quite small. It can be mounted in a small container about the size of a pager. The patient observes the alarm 80 which is preferably at least a visual alarm. A readable screen or Liquid crystal display (LCD) characters provides one suitable version. Other versions output a signal so the patient can look periodically at other LCD screen and be reassured that the prevailing multiplexer 46 be operated at a rate of about two times faster than the highest frequency component desired from the EKG signal. The Nyquist criteria in connection with the AHA definitions require sampling at least at a minimum rate just given. This sampling rate dictates the amount of data output from the spread of electrodes. In turn, the system provides the appropriately modulated RF transmission. That delivers a very large amount of data, i.e., the data transfer rate is quite high. The data transfer rate in perfect conditions might exceed about 50 kiloHertz (kHz). However, data transfer rates of this sort cannot be handled without some reduction in the data by reducing redundancy, etc. Probably the most limiting connective link reducing data content is transmission over conventional telephone lines. They are typically limited to about 4 kHz. Taking this constraint into account, the data compression scheme and the reduction of redundancy in the patient generated signal preferably provides a transmitted signal with this data content. In other words, the modulating signal encodes the signal so that it will pass through a telephone system.

The equipment 40 on the patient is preferably quite small. It can be mounted in a small container about the size of a pager. The patient observes the alarm 80 which is preferably at least a visual alarm. A readable screen or Liquid crystal display (LCD) characters provides one suitable version. Other versions output a signal so the patient can look periodically at other LCD screen and be reassured that the prevailing conditions are indicative of good health. When the problems arise, the patient may or may not have physical discomfort. If discomfort occurs, the patient is reassured by the signal on the LCD alarm 80.

Base-line Drift and DC Bias

Yet another salient feature of the invention is its capability in suppressing undesired frequency components without affecting the integrity of the desired signal. These components, as previously stated, may arise due to electrode to skin direct current offset, muscle tumor, slippage of electrodes, breathing and patient motion in general. This (i.e., filtering) is accomplished by the compression scheme mentioned previously as a bonus or a bi-product. As stated earlier, the inherent features of the compression scheme used herein is its capability of resolving signal content in time and frequency. This feature (transmission prioritization based on isolation and selectivity in time and frequency) offers great latitude in assigning low weight to the transmission coefficients that correspond to the undesired frequency components. This virtually precludes the need for the necessary filtering required on most biomedical data after acquisition and hence preserves the integrity of the significant signal components.

While the foregoing disclosure is directed to the preferred embodiment, the scope is determined by the claims which follow.

What is claimed is:

1. A method of monitoring the coronary status of a patient permitted to undertake normal activities after a cardiac episode comprising the steps of:

(a) attaching a set of electrodes to a patient after the cardiac episode to enable to undertake normal activities of life after the episode;

(b) forming a set of time dependent signals from the set of electrodes;

(c) correcting the signals for systematic errors;

(d) time multiplexing the signals;

(e) converting the multiplexed signals into digital values having a data rate;

(f) reducing the data rate while preserving patient cardiac condition in the reduced data rate;

(g) transmitting the reduced data rate patient cardiar condition;

(h) receiving at a central location the transmitted reduced data rate patient cardiac condition;

(i) wherein the steps of transmitting and receiving are limited by the pass band of a connective link between the patient and the central location;

(j) storing cardiac heart beat signal shape and condition data for the patient at the central location;

(k) electronically comparing the received reduced data rate patient cardiac condition with the stored coronary condition data to make a determination of patient cardiac condition departing from patient related cardiac heart beat signal shape; and (l) electronically responding to the step of comparing to send to the patient a signal indicative of patient cardiac conditions or indicative that medical intervention has been sent.

2. The method of claim 1 wherein the signals from the patient are multiplexed and then converted into digital signals prior to transmission.

3. The method of claim 1 wherein the signals from the patient are conditioned prior to transmission.

4. The method of claim 1 wherein the signals are corrected for drift prior to transmission.

5. The method of claim 1 wherein drift as a result of patient respiration is removed prior to transmission.

6. The method of claim 1 wherein the signals are rotated with respect to the trunk of the patient's body prior to transmission.

7. The method of claim 1 wherein the signals are shifted with respect to the patient's body prior to transmission.

8. The method of claim 1 wherein the number of electrodes connected to the patient is N, and N is a whole number integer, and the number of signals actually transmitted from the electrodes is N or less.

9. The method of claim 8 wherein N is 12 and selected electrodes are switched off.

10. The method of claim 1 including the step of transmitting to the patient a signal controlling operation of equipment so that steps 1(d) through 1(g) are carried out under remote control.

11. The method of claim 10 wherein the step of remote control switches on or off at least one electrode.

12. The method of claim 1 wherein the step of receiving the transmitted signal compares the patient coronary condition with EKG signals in a neural network and forms an indication of patient condition from operation of neural network.

13. The method of claim 12 including the preliminary step of inputting patient EKG signals.

14. The method of claim 1 wherein the step of transmitting the reduced data rate includes the additional step of transmitting to a repeater located away from the patient and away from the central location and the step of receiving includes the additional step of receiving the reduced data rate from the repeater.

15. The method of claim 14 including the step of transmitting the reduced data rate in a bandwidth fitting in a telephone line pass band.

16. The method of claim 1 wherein the patient is additionally monitored for blood oxygen content and a signal indicative of oxygen content is provided for transmission and is transmitted therewith.

17. The method of claim 16 including the step of monitoring oxygen level in four bands represented by digital data.

18. The method of claim 1 including the step of storing history of the patient and comparing the EKG obtained from that patient with the transmitted data in real time.

19. The method of claim 3 wherein said signal condition comprises correction for signal bias in a measured periodic signal by:

(a) observing the measured periodic signal over a period of time significantly larger than the period of the periodic signal;

(b) obtaining a moving average of the periodic signal from said observation; and (c) subtracting said moving average from said measured periodic signal thereby correcting said measured periodic signal for slowly varying bias changes.

20. The method of claim 4 wherein said signal drift correction comprises the steps of:

(a) forming a digital filter which has a magnitude response which is flat in band pass and which posses sharp drop off on the flanks of said band pass; and (b) passing said signals through said digital filter thereby removing relatively low frequency drift from said signal prior to transmission of said signal.

21. The method of claim 6 wherein said signals are rotated with respect to the trunk of the patients body by:

(a) defining a standard heart orientation;

(b) defining a standard array for the placement of said electrodes onto the patient's body;

(c) defining standard differences in signals from said electrodes from a heart in standard orientation;

(d) measuring differences in signals from a standard array of electrodes placed on said patient;

(e) comparing said standard differences and said measured differences to determine an actual orientation of said patient's heart; and (f) correcting said signals for non standard heart orientation based upon said comparison.

22. The method of claim 21 wherein said step of comparing involves comparing signals in the time domain.

23. A method of detecting cardiovascular difficulties with a patient having a history of such difficulties and the method comprises the steps of:

(a) obtaining EKG data of the patient at the time of difficulties;

(b) obtaining EKG data representing a set of cardiovascular difficulties indicated by EKG signals;

(c) transmitting EKG data from the patient from a remote location so that the patient EKG data is provided dynamically and with movement of the patient;

(d) processing the dynamic EKG data from the patient through a neural network dynamically with transmission of said EKG data representing a set of cardiovascular difficulties; and (e) determining from said processing the presence of a cardiovascular alarm condition and signaling the patient to seek medical assistance.

24. The method of claim 23 wherein the patient is provided with an alarm signal instructing the patient to attend a specific emergency medical facility.

25. The method of claim 23 including the step of transmitting the signal of the EKG of the patient from a remote location through a repeater system interposed between the patient and a receiver for receiving the transmitted signal so that patient care can be undertaken in emergency conditions.

26. The method of claim 23 including the step of monitoring the patient continuously as part of a recovery program for the patient so that the patient may undertake normal patient activities remote from a medical facility.

27. The method of claim 26 including the step of transmitting to the patient an alarm signal indicating to the patient that medical treatment and intervention be undertaken by the patient prior to going to an emergency medical facility.

28. The method of claim 23 including the step of directing the patient to an emergency medical facility and transmitting a signal to the emergency medical facility to indicate the patient is en route to the facility and also providing with that transmission an indication of the medical problem as indicated by the EKG of the patient.

29. A method of monitoring the coronary status of a patient permitted to undertake normal activities after a cardiac episode comprising the steps of:
   (a) attaching a set of electrodes to a patient after the cardiac episode to enable the patient to undertake normal activities of life after the episode;
   (b) forming time dependent signals from the set of electrodes;
   (c) time multiplexing the signals;
   (d) digitizing the multiplexed signals at a selected data rate;
   (e) reducing the data rate while preserving patient cardiac condition in the reduced data rate;
   (f) transmitting the reduced data rate patient cardiac condition;
   (g) receiving at a central location the transmitted reduced data rate patient cardiac condition;
   (h) wherein
      (i) the steps of transmitting and receiving are limited by the pass band of a connective link between the patient and the central location
      "(ii) the number of electrodes connected to the patient is N, and N is a whole number integer, and the number of signals actually transmitted from the electrodes is N or less, and".
      (iii) the number N remains unaltered while the signals actually transmitted are changed dependent on the medical conditions of the patient;
   (i) evaluating the received reduced data rate patient cardiac condition to dynamically make a determination of patient cardiac condition departing from patient related cardiac heart beat signal shape; and
   (j) electronically responding to the step of evaluating to send to the patient a signal indicative of patient coronary conditions or indicative that medical intervention has been initiated.

30. The method of claim 29 wherein N is 12 and selected electrodes are switched off.

31. The method of claim 29 including the step of transmitting to the patient a signal controlling operation of equipment so that steps 30(c) through 30(f) are carried out under remote control.

32. The method of claim 31 wherein the step of remote control switches on or off at least one electrode.

33. The method of claim 29 wherein the step of receiving the transmitted signal compares the patient cardiac condition with EKG signals in a neural network and forms an indication of patient condition from operation of neural network.

34. The method of claim 33 including the preliminary step of inputting patient EKG signals into a central location memory.

35. The method of claim 29 including the step of transmitting the reduced data rate in a bandwidth fitting in a telephone line pass band.

36. The method of claim 29 wherein the signals are corrected for drift prior to transmission.

37. The method of claim 29 wherein drift as a result of patient respiration is removed prior to transmission.

38. The method of claim 29 wherein the signals are rotated with respect to the trunk of the patient's body prior to transmission.

39. The method of claim 29 wherein the signals are shifted with respect to the patient's body prior to transmission.

40. The method of claim 29 wherein the patient is additionally monitored for blood oxygen content and a signal indicative of oxygen content is provided for transmission and is transmitted in four bands represented by digital data.

41. The method of claim 29 including the step of storing history of the patient and comparing the EKG obtained from that patient with the transmitted data in real time.

42. The method of claim 29 wherein the signals from the patient are conditioned prior to transmission, wherein said signal condition comprises correction for signal bias in a measured periodic signal by:
   (a) observing the measured periodic signal over a period of time significantly larger than the period of the periodic signal;
   (b) obtaining a moving average of the periodic signal from said observation; and
   (c) subtracting said moving average from said measured periodic signal thereby correcting said measured periodic signal for slowly varying bias changes.

43. The method of claim 36 wherein said signal drift correction comprises the steps of:
   (a) forming a digital filter which has a magnitude response which is flat in band pass and which posses sharp drop off on the flanks of said band pass; and
   (b) passing said signals through said digital filter thereby removing relatively low frequency drift from said signal prior to transmission of said signal.

44. The method of claim 38 wherein said signals are rotated with respect to the trunk of the patients body by:
   (a) defining a standard heart orientation;
   (b) defining a standard array for the placement of said electrodes onto the patient's body;
   (c) defining standard differences in signals from said electrodes from a heart in standard orientation;
   (d) measuring differences in signals from a standard array of electrodes placed on said patient;
   (e) comparing said standard differences and said measured differences to determine an actual orientation of said patient's heart; and
   (f) correcting said signals for non standard heart orientation based upon said comparison.

* * * * *